(12) United States Patent
Sohda et al.

(10) Patent No.: US 6,632,807 B1
(45) Date of Patent: Oct. 14, 2003

(54) (2R,4S)-(−)-[N-(4-DIETHOXYPHOSPHORYLMETHYL) PHENYL]-1,2,4,5-TETRAHYDRO-4-METHYL-7,8-METHYLENEDIOXY-5-OXO-3-BENZOTHIEPIN-2-CARBOXAMIDE

(75) Inventors: Takashi Sohda; Shigehisa Taketomi; Tsuneo Oda, all of Osaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 360 days.

This patent is subject to a terminal disclaimer.

(21) Appl. No.: 09/635,067

(22) Filed: Aug. 9, 2000

Related U.S. Application Data

(63) Continuation of application No. 08/579,731, filed on Dec. 28, 1995.

(30) Foreign Application Priority Data

Dec. 28, 1994 (JP) ............................... 6-327275

(51) Int. Cl.⁷ ........................ A61K 31/67; C07D 327/00
(52) U.S. Cl. ............................... 514/96; 549/5
(58) Field of Search ................. 549/5; 514/96

(56) References Cited

U.S. PATENT DOCUMENTS 5,071,841 A   12/1991   Sodha et al. ............... 514/96
5,158,943 A   10/1992   Sohda et al. ............... 514/96

FOREIGN PATENT DOCUMENTS

EP   0376197   7/1990
EP   0460488   12/1991
JP   294960    11/1993

OTHER PUBLICATIONS

Chemical Abstracts, vol. 121, No. 7 (Aug. 1994) 083085.

*Primary Examiner*—Deborah C. Lambkin
(74) *Attorney, Agent, or Firm*—Fitzpatrick, Cella, Harper & Scinto

(57) ABSTRACT

This invention relates to an optically active benzothiepin derivative represented by the formula:

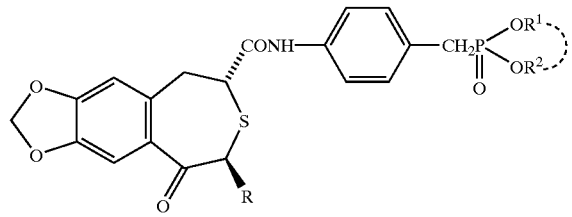

wherein R represents a lower alkyl group; $R^1$ and $R^2$ independently represent a lower alkyl group, or may bind together to form a ring, which exhibits excellent osteogenesis-promoting action and is useful as a prophylactic or therapeutic drug for bone diseases.

8 Claims, No Drawings

(2R,4S)-(−)-[N-(4-DIETHOXYPHOSPHORYLMETHYL) PHENYL]-1,2,4,5- TETRAHYDRO-4-METHYL-7,8-METHYLENEDIOXY-5-OXO-3-BENZOTHIEPIN-2-CARBOXAMIDE

This application is a continuation of application Ser. No. 08/579,731 filed Dec. 28, 1995, allowed.

TECHNICAL FIELD

The present invention relates to an optically active benzothiepin derivative possessing osteogenesis-promoting activity, bone resorption-suppressing activity and other activities, and a bone disease prophylactic or therapeutic agent comprising it as an active ingredient.

BACKGROUND OF THE INVENTION

Bone disease is a pathologic state or disease involving some symptom or risk due to quantitative reduction in bone exceeding a specified amount. Major symptoms of osteoporosis, a bone disease, are for example, spinal kyphosis, and fractures of dorsolumbar bones, vertebral centra, femoral necks, lower end of radius, ribs, and upper end of humerus. In healthy bone tissue, bone destruction occurs continuously, with a good balance between bone formation and resorption. Osteoblasts and osteoclasts, respectively, play key roles in bone formation and resorption. Deterioration of the balance therebetween results in quantitative reduction in bone. Traditionally, bone resorption suppressors, such as estrogens, calcitonin and bisphosphonates, have been primarily used to prevent and treat osteoporosis. However, these bone resorption suppressors fail to achieve satisfactory effect in some cases, due to limitations of the subject or to uncertain efficacy.

Alternatively, the present inventors have discovered a sulfur-containing heterocyclic compound possessing excellent bone resorption-suppressing activity, a compound represented by the following general formula (A) or (B), or a salt thereof (Japanese Patent Unexamined Publication Nos. 232880/1991 and 364179/1992).

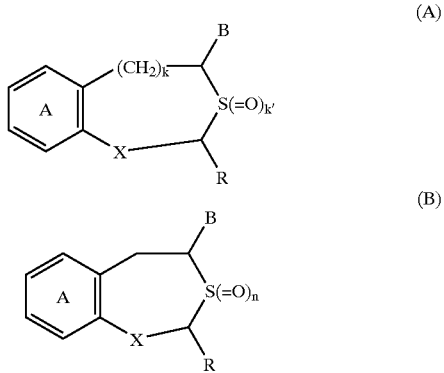

wherein ring A is a benzene ring that may be substituted; R represents a hydrogen atom or a hydrocarbon group that may be substituted; B represents a carboxyl group that may be esterified or amidated; X represents —CH(OH)— or —CO—; k represents 0 or 1, k' and n each represent 0, 1 or 2.

An example of such a compound is a compound represented by formula (C):

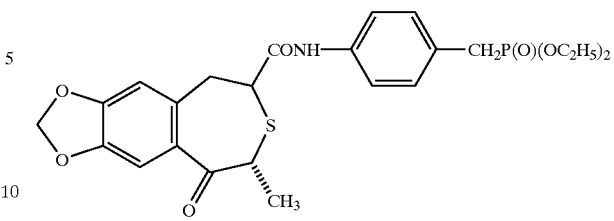

has been described.

There is a need for the development of a prophylactic or therapeutic agent having improved properties (stability, absorbability, bioavailability etc.) for clinically useful pharmaceuticals (especially oral preparations).

SUMMARY OF THE INVENTION

The present inventors conducted intensive investigation to develop a clinically more useful drug that has direct action on the bone, suppresses bone resorption, and promotes bone formation, and for the first time synthesized an optically active benzothiepin derivative represented by formula (I):

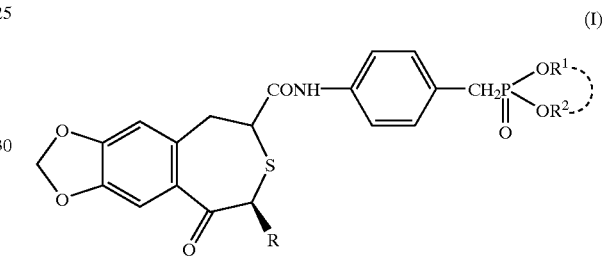

wherein R represents a lower alkyl group; $R^1$ and $R^2$ independently represent a lower alkyl group, or may bind together to form a ring; and found that this compound is unexpectedly very useful clinically among the compounds represented by formula (A) or (B) above, and is particularly effective in osteogenesis-promoting activity and oral absorbability etc. For example, the optically active benzothiepin derivative of the formula (I) is superior to the compound of the formula (C) in oral absorbability. The present inventors conducted further investigation based on this finding, and developed the present invention.

Accordingly, the present invention relates to:

(1) An optically active compound of the formula (I):

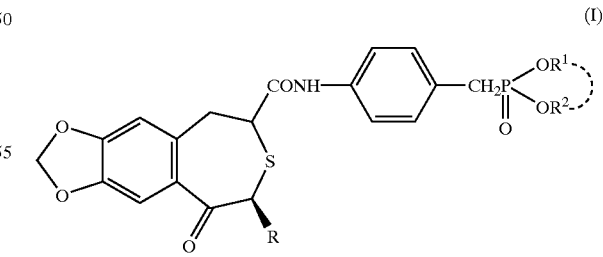

wherein R represents a lower alkyl group; $R^1$ and $R^2$ independently represent a lower alkyl group, or together represent a lower alkylene, (2) A compound according to the above (1), wherein R, $R^1$ and $R^2$ independently are a $C_{1-4}$ alkyl group, (3) A compound according to the above (1), which is (2R,4S)-(−)-N-[4-(diethoxyphosphorylmethyl)

phenyl]-1,2,4,5-tetrahydro-4-methyl-7,8-methylenedioxy-5-oxo-3-benzothiepin-2-carboxamide, (4) A method of producing an optically active compound of the formula (I):

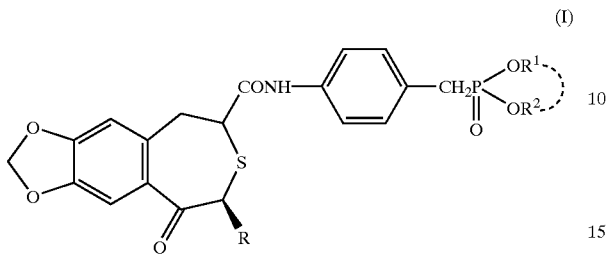

wherein R represents a lower alkyl group; $R^1$ and $R^2$ independently represent a lower alkyl group, or may bind together to form a ring, by reacting an optically active compound of the formula (II):

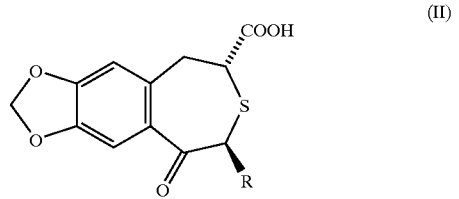

wherein R is defined as noted above, or its derivative reactive or salt at the carboxyl group, with a compound of the formula (III):

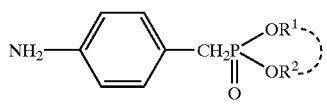

wherein $R^1$ and $R^2$ are defined as noted above, or its derivative reactive or salt at the amino group, (5) An optically active compound of the formula (II):

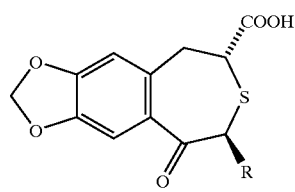

wherein R represents a lower alkyl group, or its derivative reactive or salt at the carboxyl group, (6) An osteogenesis promoter comprising an optically active compound of the formula (I) according to the above (1, (7) An osteogenesis promoter according to the above (6), which is orally absorbable, (8) A prophylactic or therapeutic agent for bone diseases comprising an optically active compound of the formula (I) according to the above (1), (9) A promoter for cure of bone fracture comprising an optically active compound of the formula (I) according to the above (1),

(10) A method of promoting osteogenesis in a mammal which comprises administering to said mammal in need an effective amount of an optically active compound of the formula (I) according to the above (1),

(11) A method of preventing or treating bone diseases in a mammal which comprises administering to said mammal in need an effective amount of an optically active compound of the formula (I) according to the above (1),

(12) A method of promoting cure of bone fracture in a mammal which comprises administering to said mammal in need an effective amount of an optically active compound of the formula (I) according to the above (1),

(13) Use of an optically active compound of the formula (I) according to the above (1) for the manufacture of an osteogenesis promoter,

(14) Use of an optically active compound of the formula (I) according to the above (1) for the manufacture of a prophylactic or therapeutic agent for bone diseases, and

(15) Use of an optically active compound of the formula (I) according to the above (1) for the manufacture of a promoter for cure of bone fracture.

With respect to the above formulas, the lower alkyl group represented by R, $R^1$ or $R^2$ is exemplified by straight chain or branched alkyl groups having 1 to 6 carbon atoms, such as methyl, ethyl, propyl, isopropyl, butyl, isobutyl, sec-butyl, tert-butyl, pentyl, isopentyl, neopentyl and hexyl. $R^1$ and $R^2$ may represent together a lower alkylene, in which case

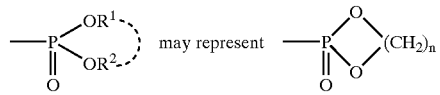

(n represents an integer from 2 to 4).

Preferably, R, $R^1$ and $R^2$ are each an alkyl group having 1 to 4 carbon atoms, such as methyl or ethyl.

The compound (I) of the present invention, an optically active compound of the (2R,4S) configuration, preferably contains substantially no compounds of the (2S,4R) configuration, and has an optical purity of nearly 100%.

Of the compounds of formula (I), (2R,4S)-(−)-N-[4-(diethoxyphosphorylmethyl)phenyl]-1,2,4,5-tetrahydro-4-methyl-7,8-methylenedioxy-5-oxo-3-benzothiepin-2-carboxamide etc. are preferred.

Compound (I) is produced by reacting an optically active compound represented by formula (II), or its derivative reactive or salt at the carboxyl group, with a compound represented by formula (III), or its derivative reactive or salt at the amino group.

Preferable derivatives of compound (III) reactive at the amino group thereof include Schiff's base type imino or enamine form tautomeric isomers resulting from reaction of compound (III) and a carbonyl compound such as aldehyde (e.g., acetaldehyde) or ketone (e.g., acetone); silyl derivatives resulting from reaction of compound (III) and a silyl compound such as bis(trimethylsilyl)acetamide, mono (trimethylsilyl)acetamide or bis(trimethylsilyl)urea; and derivatives resulting from reaction of compound (III) and phosphorus trichloride or phosgene.

Preferable derivatives of compound (II) reactive at the carboxyl group thereof include acid halides, acid anhydrides, activated amides and activated esters, all obtained by conventional methods. More specifically, such preferable reactive derivatives include acid chlorides; acid azides; mixed acid anhydrides such as those with a substitutional phosphoric acid such as dialkylphosphoric acid, phenylphosphoric acid, diphenylphosphoric acid, dibenzylphosphoric acid or halogenated phosphoric acid, or with dialkylphosphorous acid, sulfurous acid, thiosulfuric acid or sulfuric acid, or with a sulfonic acid such as methanesulfonic acid, or with an aliphatic carboxylic acid, such as acetic acid, propionic acid, butyric acid, isobutyric acid, pivalic acid, pentanoic acid, isopentanoic acid or trichloroacetic acid, or with an aromatic carboxylic acid such as benzoic acid; symmetric acid anhydrides; activated amides with imidazole, 4-substitutional imidazole, dimethylpyrazole, triazole or tetrazole; activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthio ester, p-nitrophenyl ester, p-cresylthio ester, carboxymethylthio ester, pyranyl ester, pyridyl ester, piperidyl ester and 8-quinolylthio ester; and esters with N-hydroxy compounds such as N,N-dimethylhydroxylamine, 1-hydroxy-2-(1H)-pyridone, N-hydroxysuccinimide, N-hydroxyphthalimide, 1-hydroxy-1H-benzotriazole and N-hydroxy-5-norbornane-2,3-dicarboximide. These reactive derivatives can be optionally chosen according to the type of compound (II) used.

Preferable salts of reactive derivatives of compound (II) or (III) include salts with bases, exemplified by alkali metal salts such as sodium salt and potassium salt, alkaline earth metal salts such as calcium salt and magnesium salt, ammonium salt, and organic base salts such as trimethylamine salt, triethylamine salt, pyridine salt, picoline salt, dicyclohexylamine salt and N,N-dibenzylethylenediamine salt.

This reaction is normally carried out in a commonly used solvent such as water, an alcohol such as methanol or ethanol, acetone, dioxane, acetonitrile, chloroform, methylene chloride, ethylene chloride, tetrahydrofuran, ethyl acetate, N,N-dimethylformamide or pyridine, but can be carried out in any other organic solvent, as long as it does not interfere with the reaction. These ordinary solvents may be used in mixture with water. When compound (II) or (III) is used in the form of free acid or salt thereof, this reaction is preferably carried out in the presence of an ordinary condensing agent, e.g., N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; diphenylphosphorylazide; thionyl chloride; oxalyl chloride; a lower alkyl haloformate such as ethyl chloroformate or isopropyl chloroformate; triphenylphosphine; 2-ethyl-7-hydroxybenzisoxazolium salt, 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; or in what is called Vilsmeier's reagent (as prepared by reaction of N,N'-dimethylformamide with thionyl chloride), phosgene, trichloromethyl chloroformate, phosphorus oxychloride, or the like. It is also preferable to use a condensing agent such as N,N'-dicyclohexylcarbodiimide in the presence of N-hydroxybenzotriazole or N-hydroxy-5-norbornan-endo-2,3-dicarboximide. This reaction may also be carried out in the presence of an inorganic or organic base such as alkali metal hydrogen carbonate tri(lower)alkylamine, pyridine, N-(lower)alkylmorpholine or N,N-di(lower)alkylbenzylamine. Although the reaction temperature is not subject to limitation, this reaction is normally carried out under cooling to heating (−10 to 120° C.) conditions. Reaction time is normally about 0.5 to 100 hours, preferably about 1 to 50 hours.

Compound (I) thus obtained may be isolated and purified by known means of separation and purification such as concentration, concentration under reduced pressure, solvent extraction, crystallization, recrystallization, redissolution and chromatography.

Starting compound (II) can, for example, be produced by optically resolving the racemate of compound (II) disclosed in Japanese Patent Unexamined Publication No. 364179/1992. Specifically, an optically active compound is produced by preparing a salt of the racemate of compound (II) and an optically active base (e.g., optically active α-methylbenzylamine, brucine, quinine, cinchonine), repeating fractional crystallization based on the solubility difference between the resulting diastereomers to obtain a sparingly soluble salt in pure form, then performing acid treatment. As another method, the optically active compound can be produced by esterifying the racemate of compound (II) with an optically active alcohol (e.g., optically active methyl lactate, methyl mandelate), preparing one of the resulting diastereomers of the ester in pure form on the basis of the physical property difference between the diastereomers, and then performing hydrolysis.

Compound (I), the desired compound of the present invention, can be prepared as solid preparations such as tablets, capsules, granules and powders, or liquid preparations such as syrups and injectable preparations, as formulated with pharmaceutically acceptable carriers, by conventional methods, and can be administered orally or non-orally. The content ratio of compound (I) is normally about 0.01 to 95% by weight, preferably about 0.1 to 20% by weight, relative to the entire preparation. Compound (I) is preferably used as an oral preparation.

Pharmaceutically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as required. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscarmelose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include buffer solutions of phosphates, acetates, carbonates and citrates. Preferable soothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

Since the compound represented by general formula (I) possesses potent bone resorption-suppressing activity and osteogenesis-promoting activity, and is more excellent in properties related to clinical utility, such as stability, absorbability and bioavailability, it is useful as an osteogenesis promoter and it can be used to prevent or treat various bone diseases, such as osteoporosis and bone fracture, in mammals (e.g., humans, rats, mice, cats, dogs, rabbits, bovines, swines). The compound (I) of the present invention can be safely used with low toxicity. For example, when compound (I) was orally administered to rats at a dose of 500 mg/kg/day for 2 weeks, no abnormal findings were obtained. The compound (I) is especially superior to the corresponding racemic compound in absorbability when orally administered, and is therefore useful for an orally administrable preparation.

More specifically, the optically active benzothiepin derivative relating to the present invention, represented by general formula (I), possesses excellent alkaline phosphatase induction activity, hence showing excellent osteogenesis-promoting action, and is useful as a drug for preventing or treating metabolic bone diseases, including osteoporosis. Any osteogenesis promoter comprising the compound (I) of such activity of the present invention is applicable to the treatment of bone fractures, bone defects, and bone diseases such as osteoarthritis in the field of orthopedics and periodontal diseases. Such a promoter is also expected to be effective in the field of dentistry, for repair of periodontal tissue defects due to periodontitis, stabilization of artificial tooth roots, ridge formation and repair of cleft palate etc.

When used as a prophylactic or therapeutic agent for osteoporosis, for instance, the compound represented by general formula (I) is administered at a daily dose of 5 to 1,000 mg, preferably 30 to 600 mg, as active ingredient (I), depending on patient condition and weight and method of administration, in the case of oral administration for each adult (weighing 50 kg), in 1 to 3 portions per day.

The compound (I) of the present invention can be used in combination with other bone resorption-suppresors and osteogenesis promoters such as Vitamin Ds (ex. 1α-hydroxyVitamin $D_3$, 1α,25-dihydroxyVitamin $D_3$, Flocalcitriol, Secalciferol, etc.), Calcitonins (ex. Calcitonin eel, Calcitonin salmon, Calcitonin porcine, Avicatonin, etc.), Bisphosphonic acid derivatives (ex. Etidronate, Cimadronate, Alendronate, Tiludronate, Risedronate, Clodronate, YH-529, etc.), Sex hormone related compounds (ex. Tibolone, Estradiol, Osaterone, Raloxifene, Droloxifene, Ormeloxifene, Tamoxifen, Mifepristone, etc.), Ipriflavone, Vitamin $K_2$ (ex. Menatetrenone), Sodium fluoride and PTH derivatives (ex. PTH(1-34), PTH(1-84), PTH (1-36), etc.)

DETAILED DESCRIPTION OF THE INVENTION

The present invention is hereinafter described in more detail by means of the following test example, reference example and working example. These examples, however, do not by any means limit the invention.

Test Example 1

Osteogenesis-promoting Action

Using stromal cells prepared from the femoral bone marrow of a normal rat, alkaline phosphatase activity was determined as an index of osteogenesis. Specifically, stromal cells, prepared from the femoral bone marrow of a 7-week-old male Sprague-Dawley rat by the method of Maniatopoulos et al. [Cell Tissue Research, Vol. 254, p. 317 (1988)], were cultured in an α-MEM (minimum essential medium) solution containing both dexamethasone ($10^{-7}$ M) and β-glycerophosphoric acid ($10^{-2}$ M) to obtain mineralized bone-like tissue. One week later, the test compound ($10^{-6}$ M or $10^{-5}$ M) was added to the confluent cells, followed by 10 to 14 more days of cultivation in the above culture broth. After washing with phosphate buffer, the cells were homogenized with 0.2% Nonidet P-40 and centrifuged at 3,000 rpm for 10 minutes. The resulting supernatant was assayed for alkaline phosphatase activity by the method of Lowry et al. [Journal of Biological Chemistry, Vol. 207, p. 19 (1954)]. The values obtained are given in mean ±SE in Table 1. The data were statistically analyzed by Student's t-test.

TABLE 1

| Compound | Concentration (M) | Alkaline Phosphatase Activity (nmol p-nitrophenol/min/well) |
| --- | --- | --- |
| Control | Not added | 113.7 ± 8.1 |
| Compound obtained in Example 1 | $10^{-5}$ | 1635.5 ± 169.7** |
| Compound obtained in Example 1 | $10^{-6}$ | 682.5 ± 123.2** |

*$p < 0.05$; **$p < 0.01$ vs control

From Table 1, it is seen that the optically active benzothiepin derivative relating to the present invention, represented by general formula (I), possesses excellent alkaline phosphatase induction activity, hence showing excellent osteogenesis-promoting action, and its usefulness as a drug for preventing or treating metabolic bone diseases, including osteoporosis.

Reference Example 1

A mixture of (R)-α-methoxycarbonylbenzyl ester of (2R, 4S)-(−)-1,2,4,5-tetrahydro-4-methyl-7,8-methylenedioxy-5-oxo-3-benzothiepin-2-carboxylic acid (4.18 g), acetic acid (45 ml) and concentrate hydrochloric acid (30 ml) was stirred for 30 minutes under reflux. The reaction mixture was poured into water (800 ml); the resulting crystals were collected by filtration and dissolved in ethyl acetate (150 ml). The ethyl acetate layer was washed with water and dried (using $MgSO_4$), after which the solvent was distilled off; the residual crystals were collected by filtration and washed with hexane, followed by recrystalli-zation from ethyl acetate-hexane to yield (2R,4S)-(−)-1,2,4,5-tetrahydro-4-methyl-7,8-methylenedioxy-5-oxo-3-benzothiepin-2-carboxylic acid (1.62 g, 59%). Colorless needles. Melting point 194–195° C. Optical rotation $[α]_D$ (23° C.) −210.8° (c=0.50, $CH_3OH$).

Reference Example 2

A solution of 1-ethyl-3-(3-dimethylaminopropyl) carbodiimide hydrochloride (12.59 g) in dichloromethane (200 ml) was added to a solution of (±)-trans-1,2,4,5-tetrahydro- 4-methyl-7,8-methylenedioxy-5-oxo-3-benzothiepin-2-carboxylic acid (15.34 g) and methyl (R)-(−)-mandelate (18.19 g) in N,N-dimethylformamide (DMF) (200ml), followed by the addition of 4-dimethylaminopyridine (DMAP) (3.34 g) at 0° C. This mixture was stirred at 0° C. for 1 hour and at room temperature for 15 hours, after which it was poured into water and extracted with ethyl acetate. The ethyl acetate layer was washed with water and dried (using MgSO$_4$), after which the solvent was distilled off; the residual crystals were collected by filtration and washed with ether-hexane, followed by recrystallization twice from ethyl acetate-hexane to yield (R)-α-methoxycarbonylbenzyl ester of (2R,4S)-(−)-1,2,4,5-tetrahydro-4-methyl-7,8-methylenedioxy-5-ozo-3-benzothiepin-2-carboxylic acid (4.09 g, 17%). Colorless needles. Melting point 140–141° C. Optical rotation [α]$_D$ (23° C.)−244.2° (c=0.50, CHCl$_3$).

EXAMPLE 1

(2R,4S)-(−)-N-[4-(Diethoxyphosphorylmethyl)phenyl]-1,2,4,5-tetrahydro-4-methyl-7,8-methylenedioxy-5-oxo-3-benzothiepin-2-carboxamide

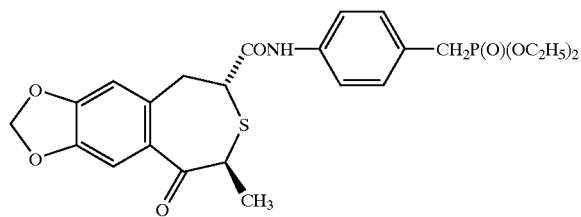

A solution of 1-ethyl-3-(3-dimethylaminopropyl)carbodiimide hydrochloride (0.39 g) in dichloromethane (7 ml) was added to a solution of (2R,4S)-(−)-1,2,4,5-tetrahydro-4-methyl-7,8-methylenedioxy-5-oxo-3-benzothiepin-2-carboxylic acid (0.47 g) and diethyl 4-aminobenzylphosphonate (0.41 g) in N,N-dimethylformamide (DMF) (7 ml) at 0° C., followed by the addition of 1-hydroxybenzo-triazole (HOBt) (0.28 g). This mixture was stirred at 0° C. for 1 hour and at room temperature (25° C.) for 15 hours, after which it was poured into water and extracted with ethyl acetate. The ethyl acetate layer was washed with water and dried (using MgSO$_4$), after which the solvent was distilled off; the residual crystals were collected by filtration, followed by recrystallization from ethyl acetate-hexane and then recrystalized from methanol-hexane to yield (2R,4S)-(−)-N-[4-(diethoxyphosphorylmethyl)phenyl]-1,2,4,5-tetrahydro-4-methyl-7,8-methylenedioxy-5-oxo-3-benzo-thiepin-2-carboxamide (0.37 g, 44%). Colorless Prisms.

Melting point 181–182° C. Optical rotation [α]$_D$ (23° C.) −187.4° (c=0.50, CHCl$_3$).

EXAMPLE 2

(2R,4S)-(−)-N-[4-(dimethoxyphosphorylmethyl)phenyl]-1,2,4,5-tetrahydro-4-methyl-7,8-methylenedioxy-5-oxo-3-benzothiepin-2-carboxamide

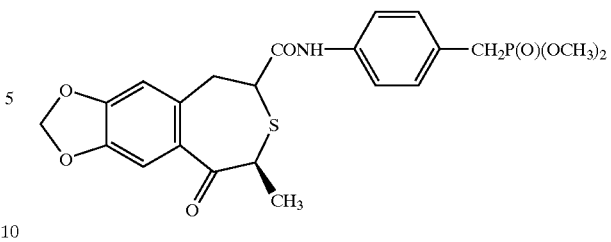

1-Hydroxybenzotriazole (HOBt) (0.51 g) and 1-ethyl-3-(3-dimethylaminopropyl)carbodiimide hydrochloride (0.69 g) were added to a solution of (2R,4S)-(−)-1,2,4,5-tetrahydro-4-methyl-7,8-methylenedioxy-5-oxo-3-benzothiepin-2-carboxylic acid (0.84 g) and dimethyl 4-aminobenzylphosphonate (0.65 g) in N,N-dimethylformamide (DMF) (10 ml) at 0° C. This mixture was stirred at 0° C. for 1 hour and at room temperature for 15 hours, after which it was poured into water and extracted with ethyl acetate-tetrahydrofuran (3:1). The ethyl acetate layer was washed successively with 1N HCl, water, a saturated sodium hydrogencarbonate solution, water and brine, and dried (MgSO$_4$), after which the solvent was distilled off. The residual solid was collected by filtration, followed by recrystallization from ethanol-hexane to yield (2R,4S)-(−)-N-[4-(dimethoxyphosphorylmethyl)phenyl]-1,2,4,5-tetrahydro-4-methyl-7,8-methylenedioxy-5-oxo-3-benzothiepin-2-carboxamide (0.92 g, 64%). Colorless needles. Melting point 198–199° C. Optical rotation [α]$_D$ (23° C.) −198.8° (c=0.50, CHCl$_3$).

EXAMPLE 3

(2R,4S)-(−)-N-[4-(tetramethylenedioxyphosphorylmethyl)phenyl]-1,2,4,5-tetrahydro-4-methyl-7,8-methylenedioxy-5-oxo-3-benzothiepin-2-carboxaminde

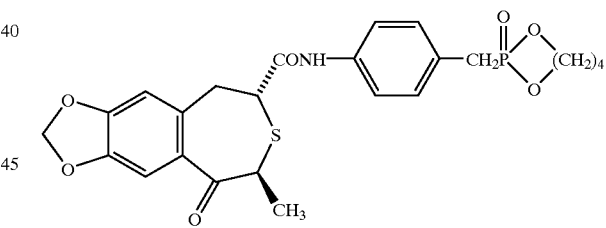

Using the same procedure as in Example 2, (2R,4S)-(−)-N-[4-(tetramethylenedioxyphosphorylmethyl)phenyl]-1,2,4,5-tetrahydro-4-methyl-7,8-methylenedioxy-5-oxo-3-benzothiepin-2-carboxamide was produced. Colorless prisms. Melting point 139–140° C. Optical rotation [α]$_D$ (23° C.) −176.2° (c=0.50, CHCl$_3$).

Preparation Examples

An osteogenesis promoter comprising an optically active compound of the formula (I) as an active ingredient can, for example, be produced with the following formulations:

1. Capsules (1) (2R,4S)-(−)-N-[4-(diethoxyphosphorylmethyl)phenyl]-    10 mg
    1,2,4,5-tetrahydro-4-methyl-7,8-methylenedioxy-5-

-continued

| | |
|---|---|
| oxo-3-benzothiepin-2-carboxamide | |
| (2) Lactose | 90 mg |
| (3) Microcrystalline cellulose | 70 mg |
| (4) Magnesium stearate | 10 mg |
| Total | 180 mg per capsule |

Components (1), (2) and (3) and a half portion of component (4) are mixed and granulated. To these granules, the remaining portion of component (4) is added, and the entire mixture is packed in a gelatin capsule.

2. Tablets

| | |
|---|---|
| (1) (2R,4S)-(-)-N-[4-(diethoxyphosphorylmethyl)phenyl]-1,2,4,5-tetrahydro-4-methyl-7,8-methylenedioxy-5-oxo-3-benzothiepin-2-carboxamide | 10 mg |
| (2) Lactose | 35 mg |
| (3) Corn starch | 150 mg |
| (4) Microcrystalline cellulose | 30 mg |
| (5) Magnesium stearate | 5 mg |
| Total | 230 mg per tablet |

Components (1), (2) and (3), a two-third portion of component (4) and a half portion of component (5) are mixed and granulated. To these granules, the remaining portions of components (4) and (5) are added, and the entire mixture is tableted by compressive tableting.

3. Injectable Preparation

| | |
|---|---|
| (1) (2R,4S)-(-)-N-[4-(diethoxyphosphorylmethyl)phenyl]-1,2,4,5-tetrahydro-4-methyl-7,8-methylenedioxy-5-oxo-3-benzothiepin-2-carboxamide | 10 mg |
| (2) Inositol | 100 mg |
| (3) Benzyl alcohol | 20 mg |
| Total | 130 mg per ampule |

Components (1), (2) and (3) are dissolved in distilled water for injection to a final quantity of 2 ml, and the solution is filled in an ampule. The entire procedure is performed aseptically.

Reference Example 3

To a suspension of (±)-3,4-dihydro-6,7-dimethyl-4-oxo-1H-2-benzothiopyran-1-carboxylic acid (27.5 g) in chloroform (200 ml) was added (S)-(-)-α-methylbenzylamine (14.1 g). After stirring at room temperature for 30 minutes, the reaction mixture was concentrated under reduced pressure. The resulting residue was dissolved in ethyl acetate (200 ml) and left at room temperature for 2 hours. The resulting crystals were collected by filtration, followed by recrystallization from chloroform-ethyl acetate and successively from chloroform-hexane to yield (S)-(-)-α-methylbenzylamine salt of (-)-3,4-dihydro-6,7-dimethyl-4-oxo-1H-2-benzothiopyran-1-carboxylic acid (15.5 g, 37%). Colorless prisms. Melting point 162–163° C. Optical rotaion $[\alpha]_D$ (23° C.) −43° (c=0.50, $CHCl_3$).

Reference Example 4

To a suspension of (±)-3,4-dihydro-6,7-dimethyl-4-oxo-1H-2-benzothiopyran-1-carboxylic acid (35.0 g) in chloroform (300 ml) was added (R)-(+)-α-methylbenzylamine (17.9 g). After stirring at room temperature for 30 minutes, the reaction mixture was concentrated under reduced pressure. The resulting residue was dissolved in ethyl acetate (200 ml) and left at room temperature for 2 hours. The resulting crystals were collected by filtration, followed by recrystallization from chloroform-ethyl acetate and successively from chloroform-hexane to yield (R)-(+)-α-methylbenzylamine salt of (+)-3,4-dihydro-6,7-dimethyl-4-oxo-1H-2-benzothiopyran-1-carboxylic acid (17.9 g, 34%). Colorless prisms. Melting point 162–163° C. Optical rotaion $[\alpha]_D$ (23° C.) +42.2° (c=0.51, $CHCl_3$).

Reference Example 5

To a suspension of (S)-(-)-α-methylbenzylamine salt of (-)-3,4-dihydro-6,7-dimethyl-4-oxo-1H-2-benzothiopyran-1-carboxylic acid (14.5 g) in ethyl acetate (100 ml) was added 2N HCl (100 ml). After the mixture was stirred at room temperature for 30 minutes, the ethyl acetate layer was collected. The ethyl acetate layer was washed with water and dried (using $MgSO_4$), after which the solvent was distilled off, followed by recrystallization from ethyl acetate-hexane to yield (-)-3,4-dihydro-6,7-dimethyl-4-oxo-1H-2-benzothiopyran-1-carboxylic acid (9.1 g, 95%). Colorless prisms. Melting point 177–178° C. Optical rotaion $[\alpha]_D$ (23° C.) −135.0° (c=0.50, $CHCl_3$).

Reference Example 6

To a suspension of (R)-(+)-α-methylbenzylamine salt of (+)-3,4-dihydro-6,7-dimethyl-4-oxo-1H-2-benzothiopyran-1-carboxylic acid (8.0 g) in ethyl acetate (100 ml) was added 2N HCl (50 ml). After the mixture was stirred at room temperature for 30 minutes, the ethyl acetate layer was collected. The ethyl acetate layer was washed with water and dried ($MgSO_4$), after which the solvent was distilled off, followed by recrystallization from ethyl acetate-hexane to yield (+)-3,4-dihydro-6,7-dimethyl-4-oxo-1H-2-benzothiopyran-1-carboxylic acid (4.55 g, 86%). Colorless prisms. Melting point 177–178° C. Optical rotaion $[\alpha]_D$ (23° C.) +136.0° (c=0.50, $CHCl_3$).

Reference Example 7

A solution of 1-ethyl-3-(3-dimethylaminopropyl) carbodiimide hydrochloride (4.89 g) in dichloromethane (80 ml) was added to a solution of (±)-1,2,4,5-tetrahydro-7,8-dimethoxy-5-oxo-3-benzothiepin-2-carboxylic acid (6.0 g) and methyl (R)-(+)-lactate (4.43 g) in N,N-dimethylformamide (DMF) (80 ml) at 0° C., followed by the addition of 4-dimethylaminopyridine (DMAP) (1.3 g). This mixture was stirred at 0° C. for 1 hour and at room temperature for 15 hours, and concentrated under reduced pressure. Ethyl acetate (500 ml) and water (500 ml) were added to the residue and then the organic layer was collected. The organic layer was washed with water and dried ($MgSO_4$), after which the solvent was distilled off; the residual solid was collected by filtration and washed with ether, followed by recrystallization twice from ethyl acetate-hexane to yield (R)-1-methoxycarbonylethyl ester of (2R)-(-)-1,2,4,5-tetrahydro-7,8-dimethoxy-5-oxo-3-benzothiepin-2-carboxylic acid (2.2 g, 28%). Colorless needles. Melting point 161–162° C. Optical rotaion $[\alpha]_D$ (16° C.) −194.1° (c=0.50, $CHCl_3$). A filtrate of the above-mentioned solid was concentrated and the resulting crystals were collected by filtration with ether-hexane, followed by recrystallization twice from ethyl acetate-hexane to yield (R)-1-methoxycarbonylethyl ester of (2S)-(+)-1,2,4,5- tetrahydro-7,8-dimethoxy-5-oxo-3-benzothiepin-2-carboxylic acid (1.6 g, 20%). Colorless Plates. Melting point 121–122° C. Optical rotaion $[\alpha]_D$ (16° C.) +234.3° (c=0.50, CHCl$_3$).

Reference Example 8

A mixture of (R)-1-methoxycarbonylethyl ester of (2R)-(−)-1,2,4,5-tetrahydro-7,8-dimethoxy-5-oxo-3-benzothiepin-2-carboxylic acid (0.5 g), acetic acid (2.5 ml) and concentrated hydrochloric acid (2.5 ml) was stirred for 30 minutes under reflux. The reaction mixture was poured into water (50 ml); the resulting crystals were collected by filtration and washed successively with water, ethanol and ether to yield (2R)-(−)-1,2,4,5-tetrahydro-7,8-dimethoxy-5-oxo-3-benzothiepin-2-carboxylic acid (0.2 g, 53%). Colorless powder. Melting point 223–224° C. Optical rotation $[\alpha]_D$ (23° C.) −190.0° (c=0.50, DMSO).

Reference Example 9

A mixture of (R)-1-methoxycarbonylethyl ester of (2S)-(+)-1,2,4,5-tetrahydro-7,8-dimethoxy-5-oxo-3-benzothiepin-2-carboxylic acid (0.7 g), acetic acid (3.5 ml) and concentrated hydrochloric acid (3.5 ml) was stirred for 30 minutes while refluxing. The reaction mixture was poured into water (70 ml); the resulting crystals were collected by filtration and washed successively with water, ethanol and ether to yield (2S)-(+)-1,2,4,5-tetrahydro-7,8-dimethoxy-5-oxo-3-benzothiepin-2-carboxylic acid (0.3 g, 56%). Colorless powder. Melting point 223–224° C. Optical rotation $[\alpha]_D$ (22° C.) +196.7° (c=0.50, DMSO).

Reference Example 10

A solution of 1-ethyl-3-(3-dimethylaminopropyl) carbodiimide hydrochloride (12.5 g) in dichloromethane (200 ml) was added to a solution of (±)-trans-1,2,4,5-tetrahydro-4-methyl-7,8-methylenedioxy-5-oxo-3-benzothiepin-2-carboxylic acid (15.34 g) and methyl (S)-(+)-mandelate (18.19 g) in N,N-dimethylformamide (DMF) (200 ml) at 0° C., followed by the addition of 4-dimethylaminopyridine (DMAP) (3.34 g). This mixture was stirred at 0° C. for 1 hour and at room temperature for 15 hours, after which it was poured into water and extracted with ethyl acetate. The ethyl acetate layer was washed with water and dried (MgSO$_4$), after which the solvent was distilled off; the residual crystals were collected by filtration and washed with ether-hexane, followed by recrystallization twice from ethyl acetate-hexane to yield (S)-α-methoxycarbonylbenzyl ester of (2S,4R)-(+)-1,2,4,5-tetrahydro-4-methyl-7,8-methylenedioxy-5-oxo-3-benzothiepin-2-carboxylic acid (4.57 g, 19%). Colorless needles. Melting point 141–142° C. Optical rotation $[a]_D$ (23° C.) +239.7° (c=0.50, CHCl$_3$).

Reference Example 11

A mixture of (S)-α-methoxycarbonylbenzyl ester of (2S,4R)-(+)-1,2,4,5-tetrahydro-4-methyl-7,8-methylenedioxy-5-oxo-3-benzothiepin-2-carboxylic acid (4.37 g), acetic acid (45 ml) and concentrate hydrochloric acid (30 ml) was stirred for 30 minutes while refluxing. The reaction mixture was poured into water (800 ml); the resulting crystals were collected by filtration and dissolved in ethyl acetate (150 ml). The ethyl acetate layer was washed with water and dried (MgSO$_4$), after which the solvent was distilled off; the residual crystals were collected by filtration and washed with hexane, followed by recrystallization from ethyl acetate-hexane to yield (2S,4R)-(+)-1,2,4,5-tetrahydro-4-methyl-7,8-methylenedioxy-5-oxo-3-benzothiepin-2-carboxylic acid (1.38 g, 48%). Colorless needles. Melting point 192–193° C. Optical rotation $[\alpha]_D$ (23° C.) +212.9° (c=0.50, CH$_3$OH).

Reference Example 12

After (−)-3,4-dihydro-6,7-dimethyl-4-oxo-1H-2-benzothiopyran-1-carboxylic acid (8.6 g) was dissolved in tetrahydrofuran (100 ml), oxalyl chloride (5.0 g) was added to the solution, followed by the addition of N,N-dimethylformamide (1 drop). After stirring at room temperature for 3 hours, the reaction mixture was concentrated under reduced pressure. The residue was dissolved in dichloromethane (30 ml) and this solution was added dropwise to a mixture of diethyl 4-aminobenzylphosphonate (8.8 g), sodium hydrogencarbonate (10.0 g) and dichloromethane (100 ml) under ice-cooling. After stirring for 30 minutes under ice-cooling, the reaction mixture was washed with water and dried (MgSO$_4$), after which the solvent was distilled off, followed by recrystallization from chloroform-hexane to yield (−)-N-[4-(diethoxyphophorylmethyl)phenyl]-3,4-dihydro-6,7-dimethyl-4-oxo-1H-2-benzothiopyran-1-carboxamide (15.4 g, 92%). Colorless needles. Melting point 175–176° C. Optical rotation $[\alpha]_D$ (23° C.) −152.0° (c=1.0, CH$_3$OH).

Reference Example 13

After (+)-3,4-dihydro-6,7-dimethyl-4-oxo-1H-2-benzothiopyran-1-carboxylic acid (8.4 g) was dissolved in tetrahydrofuran (100 ml), oxalyl chloride (5.0 g) was added to the solution, followed by the addition of N,N-dimethylformamide (1 drop). After stirring at room temperature for 3 hours, the reaction mixture was concentrated under reduced pressure. The residue was dissolved in dichloromethane (30 ml) and this solution was added dropwise to a mixture of diethyl 4-aminobenzylphosphonate (8.6 g), sodium hydrogencarbonate (8.0 g) and dichloromethane (100 ml) under ice-cooling. After stirring for 30 minutes under ice-cooling, the reaction mixture was washed with water and dried (MgSO$_4$), after which the solvent was distilled off, followed by recrystallization from chloroform-hexane to yield (+)-N-[4-(diethoxyphophorylmethyl)phenyl]-3,4-dihydro-6,7-dimethyl-4-oxo-1H-2-benzothiopyran-1-carboxamide (15.8 g, 96%). Colorless needles. Melting point 175–1760° C. Optical rotation $[\alpha]_D$ (23° C.) +155.0° (c=1.0, CH$_3$OH).

Reference Example 14

A solution of 1-ethyl-3-(3-dimethylaminopropyl) carbodiimide hydrochloride (0.149 g) in dichloromethane (3 ml) was added to a solution of (R)-(−)-1,2,4,5-tetrahydro-7,8-dimethoxy-5-oxo-3-benzothiepin-2-carboxylic acid (0.183 g) and diethyl 4-aminobenzylphosphonate (0.158 g) in N,N-dimethylformamide (DMF) (3 ml) at 0° C., followed by the addition of 1-hydroxybenzotriazole (HOBt) (0.109 g). This mixture was stirred at 0° C. for 1 hour and at room temperature for 15 hours, after which it was poured into water and extracted with ethyl acetate. The ethyl acetate layer was washed with water and dried (MgSO$_4$), after which the solvent was distilled off; the residue was treated with ethanol-isopropyl ether and the solid was removed by filtration. The filtrate was concentrated and the residual oil was subjected to silica gel column chromatography. From the fraction eluted with ethyl acetate-chloroform-methanol (15:15:1, v/v), (2R)-(−)-N-[4-(diethoxyphosphorylmethyl)

phenyl]-1,2,4,5-tetrahydro-7,8-dimethoxy-5-oxo-3-benzothiepin-2-carboxamide (0.136 g, 41%) was obtained. Colorless amorphous solid. Melting point 96–98° C. Optical rotation [α]$_D$ (23° C.) −155.0° (c=0.50, CHCl$_3$).

Reference Example 15

A solution of 1-ethyl-3-(3-dimethylaminopropyl) carbodiimide hydrochloride (0.228 g) in dichloromethane (5 ml) was added to a solution of (S)-(+)-1,2,4,5-tetrahydro-7,8-dimethoxy-5-oxo-3-benzothiepin-2-carboxylic acid (0.28 g) and diethyl 4-aminobenzylphosphonate (0.241 g) in N,N-dimethylformamide (DMF) (5 ml) at 0° C., followed by the addition of 1-hydroxybenzotriazole (HOBt) (0.167 g). This mixture was stirred at 0° C. for 1 hour and at room temperature for 15 hours, after which it was poured into water and extracted with ethyl acetate. The ethyl acetate layer was washed with water and dried (MgSO$_4$), after which the solvent was distilled off; the residue was treated with ethanol-isopropyl ether and the solid was removed by filtration. The filtrate was concentrated and the residual oil was subjected to silica gel column chromatography. From the fraction eluted with ethyl acetate-chloroform-methanol (15:15:1, v/v), (2S)-(+)-N-[4-(diethoxyphosphorylmethyl) phenyl]-1,2,4,5-tetrahydro-7,8-dimethoxy-5-oxo-3-benzothiepin-2-carboxamide (0.202 g, 40%) was obtained. Colorless amorphous solid. Melting point 97–99° C. Optical rotation [α]$_D$ (23° C.) +155.3° (c=0.50, CHCl$_3$).

Reference Example 16

A solution of 1-ethyl-3-(3-dimethylaminopropyl) carbodiimide hydrochloride (0.69 g) in dichloromethane (12 ml) was added to a solution of (2S,4R)-(+)-1,2,4,5-tetrahydro-4-methyl-7,8-methylenedioxy-5-oxo-3-benzothiepin-2-carboxylic acid (0.84 g) and diethyl 4-aminobenzylphosphonate (0.73 g) in N,N-dimethylformamide (DMF) (12 ml) at 0° C., followed by the addition of 1-hydroxybenzotriazole (HOBt) (0.51 g). This mixture was stirred at 0° C. for 1 hour and at room temperature for 15 hours, after which it was poured into water and extracted with ethyl acetate. The ethyl acetate layer was washed with water and dried (MgSO$_4$), after which the solvent was distilled off; the residual crystals were collected by filtration, followed by recrystallization from ethyl acetate-hexane and successively from methanol-hexane to yield (2S, 4R)-(+)-N-[4-(diethoxyphosphorylmethyl)phenyl]-1,2,4,5-tetrahydro-4-methyl-7,8-methylenedioxy-5-oxo-3-benzothiepin-2-carboxamide (0.62 g, 41%). Colorless prisms. Melting point 183–184° C. Optical rotation [α]$_D$ (23° C.) +190.5° (c=0.50, CHCl$_3$).

INDUSTRIAL APPLICABILITY

The compound (I) of the present invention exhibits excellent osteogenesis-promoting action, and is useful as a prophylactic or therapeutic drug for bone diseases (metabolic bone diseases, including osteoporosis, bone fractures, bone defects, and bone diseases such as osteoarthritis in the field of orthopedics); it is also effective in the field of dentistry, for repair of periodontal tissue defects, stabilization of artificial tooth roots, ridge formation and repair of cleft palate etc.

What is claimed is:

1. A pharmaceutical composition comprising optically pure (2R,4S)-(−)-[N-(4-diethoxyphosphorylmethyl) phenyl]-1,2,4,5-tetrahydro-4-methyl-7,8-methylenedioxy-5-oxo-3-benzothiepin-2-carboxamide and a pharmaceutically acceptable carrier.

2. A pharmaceutical composition according to claim 1, wherein the pharmaceutically acceptable carrier is formulated for oral administration.

3. A pharmaceutical composition according to claim 1, wherein the pharmaceutically acceptable carrier is formulated for non-oral administration.

4. A pharmaceutical composition according to claim 3, wherein the pharmaceutically acceptable carrier is formulated for injection.

5. A compound according to either of claim 1, or 2, wherein the optically pure compound is a salt which is orally absorbable.

6. A method of promoting osteogenesis in a mammal which comprises administering to said mammal in need thereof a therapeutically effective amount of optically pure (2R,4S)-(−)-[N-(4-diethoxyphosphorylmethyl)phenyl]-1,2,4,5-tetrahydro-4-methyl-7,8-methylenedioxy-5-oxo-3-benzothiepin-2-carboxamide.

7. A method of preventing or treating bone diseases in a mammal in need thereof which comprises administering to said mammal an effective amount of optically pure (2R,4S)-(−)-[N-(4-diethoxyphosphorylmethyl)phenyl]-1,2,4,5-tetrahydro-4-methyl-7,8-methylenedioxy-5-oxo-3-benzothiepin-2-carboxamide.

8. A method of promoting cure of bone fracture in a mammal in need thereof which comprises administering to said mammal a therapeutically effective amount of optically pure (2R,4S)-(−)-[N-(4-diethoxyphosphorylmethyl) phenyl]-1,2,4,5-tetrahydro-4-methyl-7,8-methylenedioxy-5-oxo-3-benzothiepin-2-carboxamide.

* * * * *